United States Patent [19]

Arpesani

[11] Patent Number: 5,047,050
[45] Date of Patent: Sep. 10, 1991

[54] INTERNAL PROSTHESIS WITH RADIOPAQUE ANNULAR PORTIONS

[76] Inventor: Alberto Arpesani, Piazza S. Angelo 1, I-20121 Milano, Italy

[21] Appl. No.: 596,409

[22] PCT Filed: Feb. 17, 1988

[86] PCT No.: PCT/EP88/00115
§ 371 Date: Oct. 14, 1988
§ 102(e) Date: Oct. 14, 1988

[87] PCT Pub. No.: WO88/06026
PCT Pub. Date: Aug. 25, 1988

Related U.S. Application Data

[63] Continuation of Ser. No. 272,747, Oct. 14, 1988, abandoned.

[30] Foreign Application Priority Data

Feb. 17, 1987 [IT] Italy .................. 19405 A/87

[51] Int. Cl.⁵ .............................. A61F 2/06
[52] U.S. Cl. ........................... 623/1; 623/11; 623/12; 623/66; 606/228
[58] Field of Search ............ 623/1, 11, 12, 13, 66; 606/228, 231

[56] References Cited

U.S. PATENT DOCUMENTS

| 3,194,239 | 7/1965 | Sullivan | 606/228 |
| 3,949,755 | 4/1976 | Vauquois | 606/231 |
| 3,993,078 | 11/1976 | Bergentz et al. | 623/1 |
| 4,041,931 | 8/1977 | Elliot et al. | 623/1 |
| 4,130,904 | 12/1978 | Whalen | 623/1 |
| 4,185,626 | 1/1980 | Jones et al. | 128/156 |
| 4,545,082 | 10/1985 | Hood | 623/1 |

FOREIGN PATENT DOCUMENTS

| 1199110 | 12/1960 | France . | |
| 8403036 | 8/1984 | PCT Int'l Appl. | 623/1 |
| 0354284 | of 1931 | United Kingdom | 128/335.5 |

*Primary Examiner*—David J. Isabella
*Assistant Examiner*—Paul Prebilic
*Attorney, Agent, or Firm*—Hedman, Gibson, Costigan & Hoare

[57] ABSTRACT

Internal prosthesis for the substitution of a part of the human body particularly in vascular surgery, which has a body (2) with a substantially tubular configuration made of plastic material tolerated by the human body and suitable for being associated by its free ends through a suture, to the ends of one or more arteries: advantageously the body defining prosthesis is radiopaque (4) so that it can be easily detected by means of an X-ray apparatus.

8 Claims, 1 Drawing Sheet

INTERNAL PROSTHESIS WITH RADIOPAQUE ANNULAR PORTIONS

This application is a continuation of U.S. Ser. No. 272,747 filed Oct. 14, 1988, now abandoned.

TECHNICAL FIELD

This invention relates to an internal prosthesis for the substitution of a part of the human body, particularly in vascular surgery.

BACKGROUND ART

As it is known, vascular surgery together with orthopedic surgery is the one which mostly profited by the introduction of prosthetic materials.

The first substitutions of arterial trunci go back to few decades ago, when the homologous graft technique was introduced, i.e. the substitution of the injured or ill part with a similar segment taken from a corpse.

Preserved human arteries had been for many years the substitutive material of choice; however, the difficulties related to the timely finding of arterial parts of special size and shape, the need to depend on "arteries banks", and the frequent technical problems related to anastomosis caused a gradual reduction in the field of their application when substitutive plastic materials were introduced on the market.

The ideal material for vascular prosthesis should include essentially the following features: it should not have any toxic, allergic or carcinogenic action, it should be pathologically inert, i.e. it should be well tolerated by the host organism, it should have a high degree of elasticity, a good porosity and high permeability to migrating cells. The last quality is absolutely necessary so that the host fibroblasts can penetrate the thickness of the prosthesis wall by fixing the same to the surrounding tissues. Similarly, inside the channel, the cells coming from the blood can adhere to the surface and form a layer defined as neointima.

Furthermore, it is necessary that the prosthesis material can be submitted to the various sterilization procedures without losing its properties and that it can be also easily shaped by means of scissors.

Sometimes it happens that, after a shorter or longer period of time, the prosthesis detaches in the suture thus causing the formation of a scar tissue that by collapsing due to the blood pressure causes a pseudoaneurism and causes the prosthesis end to come off the artery end to which it was associated.

In this type of pathology, a layer of expanded scar tissue forms around the prosthesis, thereby the arterial blood laminar flow becomes vortical thus causing a thrombi stratification within the scar tissue itself, which may be a risk for the patient.

Currently, the sole analysis techniques available to vascular surgeons in order to detect the prosthesis detachment in the suture are x-ray, echography, angiography, i.e. blood column detection, or more recently C.A.T. (Computerized Axial Tomography) and N.M.R. (Nuclear Magnetic Resonance).

In the case of angiography, the detection of the blood column does not always allow the pathology to be detected, by x-ray the evidence of pathology is almost impossible as the prostheses currently available on the market are not radiopaque; on the contrary, by C.A.T. or N.M.R. and by echography a section detection of the pathology is possible even if it is very difficult to detect and quantify any displacement of the prosthesis end from the artery end.

DISCLOSURE OF THE INVENTION:

The main object of this invention is to overcome the above-mentioned drawbacks by making an internal prosthesis for the substitution of a part of the human body particularly in vascular surgery, which allows the detection of its positioning by means of a simple x-ray apparatus.

Within this scope of the invention, a relevant object of the invention is to design a prosthesis allowing the detection and the quantification of its displacement from the artery to which it was connected.

Another object of the invention is to make a prosthesis which, even if it allows an easier detection, has the same functional properties of the current prostheses.

The above and other objects are fulfilled by means of an internal prosthesis for the substitution of a part of the human body particularly in vascular surgery, having a body with a substantially tubular configuration of plastic material well-tolerated by the human body and being suitable for being associated by its free ends, by means of a cross or oblique suture, to the ends of one or more arteries, characterized in that said body is radiopaque and/or in that said body has radiopaque surface portions developing without discontinuity over its entire surface.

BRIEF DESCRIPTION OF THE DRAWING

Further features and advantages of the invention will be better understood from the description of a preferential embodiment, which is merely illustrative, of the prosthesis in accordance with the invention, shown by way of example and not limited thereto in the enclosed drawings in which.

WAYS OF CARRYING OUT THE INVENTION

With particular reference to the above-mentioned Figures, the prosthesis in accordance with the invention, globally referred to under the reference number 1, has a body, generally referred to as 2, which generally is made of plastic material tolerated by the human body such as some acrylic resins and some ethylene polymers.

Figure 1A:
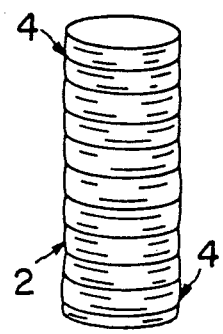
FIG. 1a shows one configuration that the prosthesis of the invention may have.
Figure 1B:
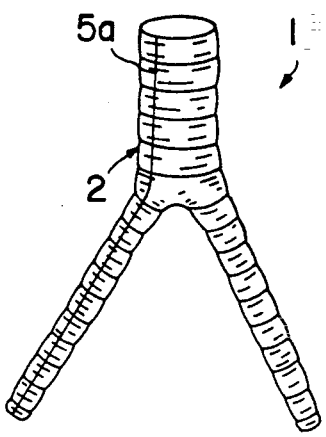
FIG. 1b shows another configuration that the prosthesis of the invention may have.
Figure 1C:
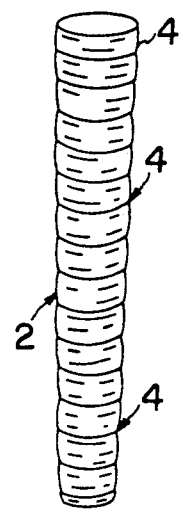
FIG. 1c shows still another of the various configurations that the prosthesis of the invention may have.
Figure 2:
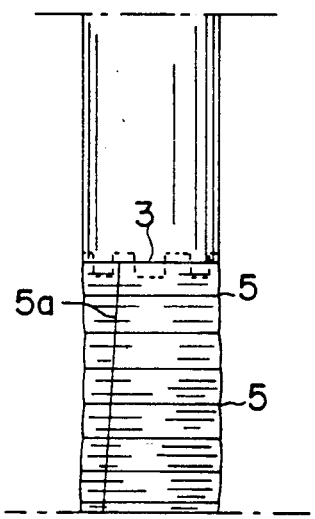
FIG. 2 is a schematic view of the prosthesis suture with an artery according to the well-known technique.

Suitably, according to the type of vascular surgery to be performed, the body 2 has different configurations that are all substantially tubular and that in particular might be also cylindrical, "Y"-shaped, or tapered, as shown by way of example in FIG. 1, and that are able to possess among the basic requirements a high degree of elasticity, a good porosity and enough permeability to migrating cells.

Advantageously, in accordance with the invention, the body 2 is also radiopaque so that the vascular surgeon can accurately determine its position relatively to one or more ends 3 of the arteries by means of an x-ray apparatus of standard type and/or while making the angiography.

More in details, the body 2, defining the prosthesis, can be for instance made radiopaque, as we already said, by means of a suitable processing or by coating or inserting in its wall a radiopaque fabric.

In a preferred embodiment, but not limited thereto, the body 2 has radiopaque surface portions developing without discontinuity over its entire surface, more precisely said radiopaque portions, generally referred to as elements 4 and 5, show an annular development and are preferably but not necessarily defined for example by a filiform element 5 or by a fabric having radiopacity properties.

Suitably, the radiopaque portions 4 are reciprocally equidistant and parallel along the entire development of the body 2 so that the detection of the existing type of pathology can be extremely easy thus allowing the carrying on of any further investigation and of the treatment, if any.

Figure 3:
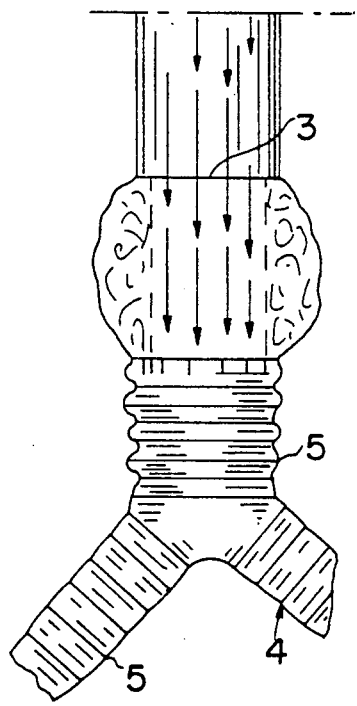
FIG. 3 shows the pathology determined by the detachment of the prosthesis from the artery.
Figure 4:
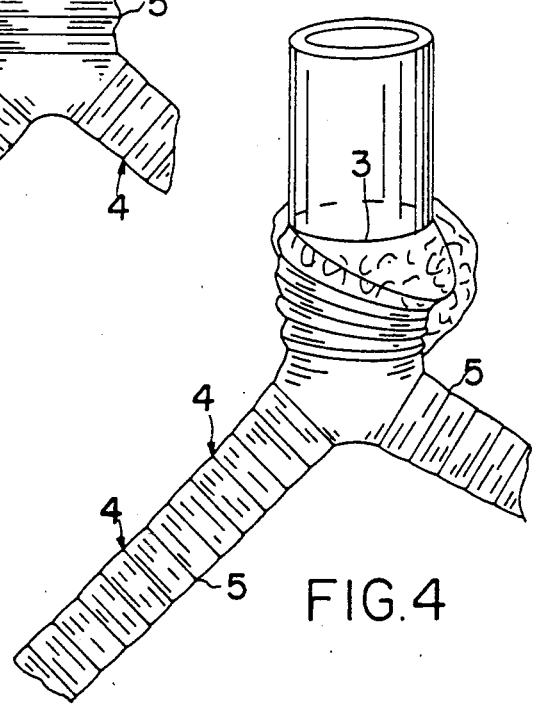
FIG. 4 shows a variant of the pathology shown in FIG. 3.

As the prosthesis relatively to the end of the artery or arteries can show a total or partial detachment, as shown for example in FIG. 4, causing a pseudoaneurism due to the coming off of the ends of the artery and of the prosthesis, such coming off being filled by an expanded scar tissue that is not blood-pressure resistent, as it is shown for example in FIG. 3, the parallelism and equidistance of the radiopaque portions having an annular development along the entire body 2 allow to determine accurately in which of the above-mentioned cases the prosthesis is relatively to the artery and therefore allow the vascular surgeon to act accordingly.

Advantageously, the radiopaque portions have the same functional properties of the body 2 so that the special nature of the prosthesis is not altered; moreover, the radiopaque portions are sensorially perceptible and more precisely they are visible to the naked eye so to make the surgeon's task easier during vascular surgery, i.e. during the execution of the anastomosis at the level of one of the radiopaque rings.

Finally, the radiopaque portions can also have a stain different from the stain of the body 2 and/or from each other in order to better stand out on the same.

Furthermore, it shall be specified that beside the radiopaque portions having an annular development, the body 2 can have a filiform element 5a extending along the longitudinal development of the body 2 and its branches.

The operation of the prosthesis in accordance with the invention is evident from what has been described and illustrated herein; in particular, it can be specified that during vascular surgery the surgeon will cut, according to the needs, a prosthesis length just close to one of the radiopaque portions with annular development so that the latter is at the connection with the artery end and allows later the accurate detection of the connection between artery and prosthesis.

In practice, it has been noticed that the prosthesis in accordance with the invention turns out to be extremely advantageous as it allows, by means of a simple x-ray apparatus now existing in all hospital centers, its detection and correct positioning relatively to the artery to which it was previously connected.

The invention as herein disclosed is subject to many variations and changes all within the scope of the invention; moreover, all details can be replaced by technically equivalent elements.

In practice, all the materials used as well as the size can be of any type according to the needs and to the state of the art.

I claim:

1. A prosthetic device for vascular surgery, comprising a substantially tubular body including plastic material and tolerated by the human body, wherein said tubular body has free ends for attaching to at least one artery, and wherein said tubular body has radiopaque annular portions which are continuous over the entire surface of said tubular body and spaced equidistant along said tubular body for detection of said tubular body by X-rays wherein the radiopaque annular portions do not alter the functional properties or special nature of the prosthetic device.

2. The device of claim 1 wherein said radiopaque annular portions are integral to said body.

3. The device of claim 1 wherein said radiopaque annular portions comprise a filament.

4. The device of claim 1 wherein said radiopaque annular portions comprise a fabric.

5. The device of claim 4 wherein said radiopaque annular portions are visible.

6. The device of claim 5 wherein each of said radiopaque annular portions has a different stain.

7. A prosthetic device for vascular surgery, comprising a substantially tubular body including plastic material and tolerated by the human body, wherein said tubular body has free ends for attaching to at least one artery, and wherein said tubular body has radiopaque similar portions integral to said body wherein said radiopaque portions are visible and continuous over the entire surface of said tubular body and spaced equidistant along said tubular body for detection of said tubular body by X-rays and wherein each of said radiopaque portions has a different stain.

8. The device of claim 7 wherein said body has a stain and said stain of said body is different from said stains of said radiopaque portions.

* * * * *